United States Patent [19]
Mitra

[11] Patent Number: 5,935,535
[45] Date of Patent: *Aug. 10, 1999

[54] DISPENSING APPARATUS

[75] Inventor: Sumita B. Mitra, West St. Paul, Minn.

[73] Assignee: 3M Innovative Properties Company, St. Paul, Minn.

[*] Notice: This patent issued on a continued prosecution application filed under 37 CFR 1.53(d), and is subject to the twenty year patent term provisions of 35 U.S.C. 154(a)(2).

[21] Appl. No.: 08/706,456

[22] Filed: Sep. 4, 1996

[51] Int. Cl.$^6$ .............................. B01D 11/02; B43K 5/02
[52] U.S. Cl. ......................... 422/261; 401/40; 401/118; 401/137; 526/318.4
[58] Field of Search ................... 526/318.4; 401/118, 401/137, 40; 422/261

[56]        References Cited

U.S. PATENT DOCUMENTS

| 2,522,617 | 9/1950 | Ijams ........................................ 401/40 |
| 3,760,503 | 9/1973 | Baskas ....................................... 32/17 |
| 4,159,570 | 7/1979 | Baskas et al. ............................... 32/66 |
| 4,215,985 | 8/1980 | Madlener .................................. 433/90 |
| 4,719,149 | 1/1988 | Aasen et al. ............................. 428/473 |
| 4,758,643 | 7/1988 | Tanaka et al. ....................... 526/318.4 |
| 4,995,540 | 2/1991 | Colin et al. .............................. 222/132 |
| 5,130,347 | 7/1992 | Mitra ....................................... 522/149 |
| 5,172,807 | 12/1992 | Dragan et al. .......................... 206/219 |
| 5,195,663 | 3/1993 | Martin et al. . |
| 5,221,202 | 6/1993 | James . |
| 5,328,947 | 7/1994 | Taguchi et al. ....................... 526/318.4 |
| 5,348,154 | 9/1994 | Jacobs et al. . |
| 5,377,823 | 1/1995 | Steen et al. . |
| 5,429,229 | 7/1995 | Chester et al. . |
| 5,490,736 | 2/1996 | Haber et al. .............................. 401/40 |
| 5,525,647 | 6/1996 | Eichmiller .............................. 523/105 |
| 5,525,648 | 6/1996 | Aasen et al. ............................ 523/116 |

FOREIGN PATENT DOCUMENTS

| 0 234 934 | 2/1987 | European Pat. Off. . |
| 54-20451 | 2/1979 | Japan ................................. 526/318.4 |
| 54-33321 | 10/1979 | Japan ................................. 526/318.4 |
| WO 93/12760 | 12/1992 | WIPO . |

*Primary Examiner*—Bernard Lipman
*Assistant Examiner*—N. Sarofim
*Attorney, Agent, or Firm*—Dale A. Bjorkman

[57]        ABSTRACT

An apparatus for dispensing a predetermined quantity of a multi-component composition in which the composition includes a first component and a second component in a predetermined weight to weight ratio, and in which the first component and said second component undergo an undesirable chemical reaction with each other when brought into contact with each other. The apparatus includes a receptacle for storing one of the first component or the second component that is adapted to receive the other of the first component or the second component from a separate source to form the predetermined quantity of multi-component composition having the first component and the second component in a predetermined weight to weight ratio.

19 Claims, No Drawings

DISPENSING APPARATUS

BACKGROUND OF THE INVENTION

The invention relates to dispensing a predetermined quantity of a multi-component composition in which the components undergo an undesirable chemical reaction with each other when brought into contact with each other.

Dental primer-adhesive compositions are applied to a tooth prior to addition of a material such as a dental restorative or composite in order to enhance adhesion between the tooth and the restorative or composite. Examples of useful primer-adhesive composition, described in Aasen et al., U.S. Pat. No. 4,719,149 and Aasen et al., U.S. Pat. No. 5,525,648, hereby incorporated by reference, feature water, an acid, and one or more polymerizable, film-forming components (i.e., components that form a film upon polymerization); an actinic radiation-sensitive curative and a non-polymerizable polymer may be included as well. The purpose of the acid is to etch the tooth surface. The film-forming component, upon polymerization, forms a film on the etched tooth surface to enhance adhesion between the tooth and a subsequently applied restorative or composite. A particularly useful primer-adhesive composition includes water, maleic acid, hydroxy ethyl methacrylate ("HEMA"), a polyalkenoic acid having polymerizable groups (e.g., acrylate or methacrylate groups), and curative.

SUMMARY OF THE INVENTION

In a first aspect, the invention features an apparatus for dispensing a predetermined quantity of a primer-adhesive composition that includes a first component and a second component in a predetermined weight to weight ratio in which the first component and the second component undergo an undesirable chemical reaction with each other when brought into contact with each other. The apparatus includes a receptacle for storing one of the first component or the second component, the receptacle being adapted to receive the other of the first component or the second component from a separate source to form the predetermined quantity of primer-adhesive composition in which the first and second components are present in the predetermined weight to weight ratio.

In preferred embodiments, the composition is a dental primer-adhesive composition. The receptacle preferably stores the first or second component of the composition in the form of a solid.

In one preferred embodiment, the first component is an acid (e.g., an organic acid) and the receptacle stores the acid, e.g., in the form of a solid adhered to a surface of the receptacle. Examples of suitable acids include mineral acids, carboxylic acids, sulfonic acids, and phenols, as well as combination thereof. A preferred acid is maleic acid.

The second component preferably includes at least one polymerizable component. The receptacle may store the polymerizable component. Examples of suitable polymerizable components include alkyl acrylates, alkyl methacrylates, and combinations thereof. One example of a preferred polymerizable component is hydroxy ethyl methacrylate. A second example is a polyalkenoic acid having one or more addition polymerizable reactive groups (e.g., vinyl groups such as acrylate or methacrylate groups).

One example of a preferred primer-adhesive composition includes maleic acid and hydroxy ethyl methacrylate. A second example of a preferred primer-adhesive composition includes maleic acid, hydroxy ethyl methacrylate, and a polyalkenoic acid having one or more addition polymerizable reactive groups.

The receptacle can take many forms. Preferred receptacles include those in the form of a well, brush, sponge, or pledget.

In a second aspect, the invention features a kit for dispensing a predetermined quantity of the above-described primer-adhesive composition that includes a first receptacle for storing one of the first component or the second component, and a second receptacle for storing the other of the first component or the second component, where the first receptacle is adapted to receive the other of the first component or the second component from the second receptacle to form the predetermined quantity of primer-adhesive composition.

In preferred embodiments, the primer-adhesive composition is a dental primer-adhesive composition. The first component preferably includes an acid and the second component preferably includes at least one polymerizable component. The first receptacle preferably stores the acid (e.g., in the form of a solid adhered to a surface of the first receptacle) and the second receptacle stores the polymerizable component. Preferred forms for the first receptacle include a well, brush, sponge, or pledget.

In a third aspect, the invention features a method for dispensing a predetermined quantity of the above-described primer-adhesive composition that includes contacting a predetermined quantity of one of the first component or the second component stored in a receptacle with a predetermined quantity of the other of the first component or the second component. The relative quantities of the first and second components are selected to form the predetermined quantity of the above-described primer-adhesive composition.

In a fourth aspect, the invention features an apparatus for dispensing a predetermined quantity of a multi-component composition that includes a first component and a second component in a predetermined weight to weight ratio in which the first component and the second component undergo an undesirable chemical reaction with each other when brought into contact with each other. The apparatus includes a receptacle for storing one of the first component or the second component, and is adapted to receive the other of the first component or the second component from a separate source to form the predetermined quantity of multi-component composition in which the first component and the second component are in the predetermined weight to weight ratio.

The invention provides a simple and effective means for dispensing a multi-component composition such as a dental primer-adhesive composition in which at least some of the individual components undergo an undesirable chemical reaction with each other upon contact with each other. The invention is particularly useful in the context of dental primer-adhesive compositions containing, e.g., maleic acid and one or more acrylate or methacrylate-containing polymerizable components such as hydroxyethyl methacrylate in which the maleic acid attacks and degrades the polymerizable component, thereby decreasing the shelf-life of the composition and the amount of polymerizable material available for the polymerization reaction. Storing a predetermined amount of one of the components in a separate receptacle avoids the shelf-life instability associated with storing the components together. Moreover, because the components are pre-measured, they are readily dispensed in desired quantities, thereby ensuring that the final composition contains the individual components in the requisite weight to weight ratio. Ease of storage and application are further enhanced when the receptacle contains one of the components in the form of a solid, e.g., adhered to a surface of the receptacle.

Other features and advantages of the invention will be apparent from the following description of the preferred embodiments thereof, and from the claims.

DETAILED DESCRIPTION

The dispensing apparatus includes a receptacle for storing a pre-determined quantity of one component of a multi-component composition containing at least two components which undergo an undesirable chemical reaction with each other when they come in contact with each other. Such undesirable chemical reactions degrade one or more of the components, thereby impairing the utility of the composition. Examples of undesirable chemical reactions include hydrolysis, oxidation, and reduction reactions, as well as other reactions which cause degradation.

The component is applied to the receptacle by impregnating, coating, precipitating, saturating, or otherwise imbuing the receptacle with a pre-determined amount of the desired component. For example, the component can be applied by dissolving the component in a solvent, incorporating the resulting solution into or onto a surface of the receptacle, and flashing off the solvent to yield the component in the form of a solid residue adhered to the receptacle. The amount of the component, as well as the second component, is selected to yield a desired quantity of the final composition (e.g., a quantity suitable for a single use) in which the components are present in a specific weight to weight ratio.

The receptacle may take many forms. Generally, any device that can store a pre-determined quantity of a component, either in liquid or solid form, and which can conveniently serve to mix and optionally apply the composition once the second component has been added can be used. Preferably, the receptacle is a different color from the component stored in the receptacle.

One example of a suitable receptacle is a mixing well or container, e.g., made from a plastic such as polystyrene. The component is applied to the surface of the well. The well can then be sealed, e.g., with a removable cover or film, until needed, and then re-sealed, if desired. For example, the cover can be slidably attached to a substrate housing the well. Alternatively, the cover can be peelably or hingedly attached to the substrate. Furthermore, the cover can be designed to transmit at least a portion of the visible light spectrum, without transmitting a substantial portion of actinic radiation that might otherwise prematurely cure any photocurable material in the well.

The wells may be supplied individually or in packs containing multiple wells. In the case of the latter, the individual wells may be separated, e.g., by perforations to facilitate use.

Particular examples of suitable well configurations are described in the following U.S. patents, all of which are incorporated by reference: Steen et al., U.S. Pat. No. 5,377,823; James, U.S. Pat. No. 5,221,202; Chester et al., U.S. Pat. No. 5,429,229; and Jacobs et al., U.S. Pat. No. 5,348,154.

Another example of a suitable receptacle is a mixing and dispensing device described in Martin et al., U.S. Pat. No. 5,195,663, hereby incorporated by reference. This device features a receptacle adapted to receive a removable capsule. The capsule has a single chamber and piston with a handle portion that is movable within the confines of the chamber. One of the components is placed in the chamber in the form of a tablet. The piston is then separated from the capsule when it is desired to add the second component (in the form of a liquid).

Another example of a suitable receptacle is a brush having either hollow or solid lumens. The component is incorporated into the interior of the lumen (in the case of hollow lumens) or onto the surface of the lumen (in the case of solid lumens).

Another example of a suitable receptacle is a sponge or absorptive pledget, optionally positioned on the end of a wand. The component is incorporated into the pores of the sponge or pledget by imbibing the sponge with a solution containing the component.

At the desired time, a pre-determined amount of the second component of the composition is added to the receptacle to form the composition. In the case of a mixing well or container, the second component (again, in liquid or solid form) is added to the first component already contained in the well. The two are mixed together, with the addition of solvent, if necessary, to generate the composition. For example, the components can be mixed together using a brush, which can then be used to apply the resulting composition to the desired substrate.

The apparatus is particularly useful for dispensing dental primer-adhesive compositions containing an acid and at least one polymerizable component in which the acid degrades the polymerizable component when the two are brought into contact with each other.

The acid is preferably soluble in the polymerizable component. A "soluble" acid is an acid that dissolves in the polymerizable component to form a substantially homogeneous liquid mixture. Moreover, the acid preferably has a $pK_a$ in water that is less than or equal to that of phenol, e.g., between about +10 and −10, more preferably between about −7 and about +5.

Examples of suitable acids include mineral acids, carboxylic acids, sulfonic acids, and phenols, with carboxylic acids, alkylsulfonic acids, and arylsulfonic acids being preferred. Specific examples include HBr, HCl, $HNO_3$, formic acid, trifluoroacetic acid, trichloroacetic acid, dichloroacetic acid, chloroacetic acid, tribromoacetic acid, dibromoacetic acid, bromoacetic acid, acetic acid, alpha-chloropropionic acid, propionic acid, maleic acid, fumeric acid, citraconic acid, pivalic acid, methacrylic acid, acrylic acid, trihydroxybenzoic acid, benzoic acid, camphorquinonesulfonic acid, camphorsulfonic acid, toluenesulfonic acid, trifluoromethanesulfonic acid, benzenesulfonic acid, 2-hydroxy-4-methoxybenzophenone-5-sulfonic acid, 2-acrylamido-2-methylpropane sulfonic acid, 2-naphthalene sulfonic acid, para-nitrophenol, 2,4-dinitrophenol, and phenol. Mixtures of such acids can be used if desired. Maleic acid is particularly preferred because of its ability to etch teeth.

The polymerizable component preferably is a water-dispersible material capable of forming a continuous or semi-continuous film on the surface of hard tissue. As used herein, a "water-dispersible" material has a water dispersibility or more preferably a water solubility of at least about 5 weight percent. Most preferably, the material can be mixed with water in all proportions. "Dispersibility" means the capability of a substance to form a dispersion, i.e., a two-phase system where one phase consists of finely divided particles (often in the colloidal size range) distributed throughout a bulk substance, the particles being the disperse or internal phase and the bulk substance the continuous or external phase.

Preferred polymerizable components contain one or more substances having a sufficient number of water-solubilizing groups such as hydroxyl groups, carboxyl groups, sulfonic acid groups, cationic salts (e.g., ammonium, phosphonium or sulfonium groups), amide linkages or polyether linkages to render the polymerizable component water-soluble. The polymerizable component preferably wets the hard tissue and, more preferably, has a sufficiently low viscosity to enable it to flow into interstices that already exist in the surface of the tissue or that are created therein by the action of the acid.

One class of suitable polymerizable components includes monomers such as 2-hydroxyethylacrylate, 2-hydroxyethylmethacrylate ("HEMA"), 2- and 3-hydroxypropylacrylate and methacrylate, 1,3- and 2,3-dihydroxypropylacrylate and methacrylate, 2-hydroxypropyl-1,3-diacrylate and dimethacrylate, 3-hydroxypropyl-1,2-diacrylate and dimethylacrylate, pentaerythritol diacrylate and dimethacrylate, acrylic acid, methacrylic acid, 2-trimethylammonium ethylmethacrylic chloride, 2-acrylamido-2-methylpropanesulfonic acid, acrylamide, methacrylamide, 2-hydroxyethylacrylamide and methacrylamide, N,N-bis(2-hydroxyethyl)acrylamide and methacrylamide, N-alkyl-N-hydroxyethyl acrylamides and methacrylamides, 2- and 3-hydroxypropylacrylamide and methacrylamide, methacrylamidopropyltrimethylammonium chloride, polyethyleneglycol (400) diacrylate and dimethacrylate, and mixtures thereof. The preferred monomer is HEMA.

A second class of polymerizable components includes polymers of ethylenically unsaturated monomers having addition polymerizable reactive groups (e.g., vinyl groups such as acrylates and methacrylates). Particularly preferred are polymers containing such reactive groups which further contain functional groups having an affinity for hard tissue. Such groups include, for example, beta-dicarbonyl groups and carboxylic acid groups. These polymers are referred to as "polyalkenoic acids" and are described, e.g., in Aasen et al., U.S. Pat. No. 5,525,648 and Mitra, U.S. Pat. No. 5,130,347, both of which are incorporated by reference.

The composition may contain more than one polymerizable component. For example, the composition may contain a polymerizable monomer such as HEMA and a polyalkenoic acid having polymerizable acrylate or methacrylate groups.

Other ingredients which may be combined with the polymerizable component(s) include actinic radiation-sensitive curatives, and co-solvents such as water, alcohols (e.g., methanol, ethanol, 1-propanol, 2-propanol, and 2-methyl-2-propanol), ketones (e.g., acetone and methylethyl ketone), aldehydes (e.g., formaldehyde, acetaldehyde, propionaldehyde, acrolein, glutaraldehyde and 2-hydroxyadipaldehyde), amides (e.g., acetamide), tetrahydrofuran, and dimethylsulfoxide. Polymers without polymerizable groups such as polyesters, polyamides, polyethers, polyethylene glycol, polysaccharides, cellulosic polymers, polypropylene, polyacrylonitrile, polyurethane, polyvinyl chloride, polymethyl methacrylate, phenol-formaldehyde polymers, melamine-formaldehyde polymers, and urea-formaldehyde polymers, as well as combinations thereof, may be included as well.

An example of a typical dental primer-adhesive has the following composition (where all percentages are weight percentages unless otherwise noted):

Solution A: 10–15% Polyalkenoic Acid Copolymer*
  20–40% HEMA
  1–90% Ethanol
  Curatives (camphorquinone and diphenyliodonium hexafluorophosphate) (less than 1%)
*Ethylenically unsaturated acidic copolymer prepared like the precipitated dry polymer of Example 11 of U.S. Pat. No. 5,130,347, hereby incorporated by reference.
Solution B: 2–20% Maleic acid
  98–80% Deionized Water The invention will now be further described by way of the following example.

EXAMPLE 1

A first solution ("Solution A") was prepared by combining 6.8% polyalkenoic copolymer prepared like the precipitated dry polymer of Example 11 of U.S. Pat. No. 5,130,347, 22% HEMA, 21.2% ethanol, 50% deionized water, and curatives (CPQ and DPI). A second solution ("Solution B") was prepared by combining 5% maleic acid in water. One drop of Solution B was placed in each of several black polystyrene wells. The solvent was then flashed off by placing each of the wells on a platen heated to 30° C. or by maintaining the wells at room temperature overnight to yield wells coated with solid maleic acid.

To each well was added a drop of Solution A. The solid maleic acid dissolved readily after mixing with a brush. The resulting mixture was then applied to a tooth, after which a restorative paste was applied to the treated tooth.

Other embodiments are within the following claims.

What is claimed is:

1. An apparatus for dispensing a predetermined quantity of a primer-adhesive composition,
   said primer-adhesive composition comprising an acid and a second component in a predetermined weight to weight ratio in which said acid and said second component undergo an undesirable chemical reaction with each other when brought into contact with each other,
   said apparatus comprising a receptacle comprising a predetermined amount of said acid adhered to said receptacle, said acid being in the form of a solid, said receptacle being adapted to receive said second component from a separate source to form said predetermined quantity of primer-adhesive composition comprising said acid and said second component in said predetermined weight to weight ratio.

2. The apparatus of claim 1, wherein said composition comprises a dental primer-adhesive composition.

3. The apparatus of claim 1, wherein said acid comprises an organic acid.

4. The apparatus of claim 1, wherein said acid comprises a mineral acid, a carboxylic acid, a sulfonic acid, a phenol, or combination thereof.

5. The apparatus of claim 1, wherein said acid comprises maleic acid.

6. The apparatus of claim 1, wherein said second component comprises at least one polymerizable component.

7. The apparatus of claim 1, wherein said second component comprises a polymerizable component and said polymerizable component is adhered to a surface of said receptacle.

8. The apparatus of claim 1, wherein said second component comprises an alkyl acrylate, an alkyl methacrylate, or combination thereof.

9. The apparatus of claim 1, wherein said second component comprises hydroxy ethyl methacrylate.

10. The apparatus of claim 1, wherein said second component comprises a polyalkenoic acid having one or more addition polymerizable reactive groups.

11. The apparatus of claim 1, wherein said acid comprises maleic acid and said second component comprises hydroxy ethyl methacrylate.

12. The apparatus of claim 1, wherein said acid comprises maleic acid and said second component comprises a mixture of hydroxy ethyl methacrylate, and a polyalkenoic acid having one or more addition polymerizable reactive groups.

13. The apparatus of claim 1, wherein said receptacle is in the form of a well.

14. The apparatus of claim 1, wherein said receptacle is in the form of a brush.

15. The apparatus of claim 1, wherein said receptacle is in the form of a sponge.

16. The apparatus of claim 1, wherein said receptacle is in the form of a pledget.

17. An apparatus for dispensing a predetermined quantity of a multi-component composition, said composition comprising an acid and a second component in a predetermined weight to weight ratio in which said acid and said second component undergo an undesirable chemical reaction with each other when brought into contact with each other, said apparatus comprising a receptacle comprising said acid adhered to a surface of said receptacle, said acid being in the form of a solid, said receptacle being adapted to receive said second component from a separate source to form said predetermined quantity of multi-component composition comprising said acid and said second component in said predetermined weight to weight ratio.

18. The apparatus of claim 1, wherein said receptacle is selected from the group consisting of a well, a brush, a sponge, a pledget or a combination thereof.

19. An apparatus for dispensing a predetermined quantity of a primer-adhesive composition, said primer-adhesive composition comprising a polymerizable component and a second component in a predetermined weight to weight ratio in which said polymerizable component and said second component undergo an undesirable chemical reaction with each other when brought into contact with each other, said apparatus comprising a receptacle comprising said polymerizable component adhered to said receptacle, said polymerizable component being present on said receptacle in a predetermined amount, said receptacle being adapted to receive said second component from a separate source to form said predetermined quantity of primer-adhesive composition comprising said polymerizable component and said second component in said predetermined weight to weight ratio.

* * * * *